(12) United States Patent
Sherman

(10) Patent No.: US 6,713,495 B1
(45) Date of Patent: Mar. 30, 2004

(54) MAGNESIUM OMEPRAZOLE

(75) Inventor: Bernard Charles Sherman, 50 Old Colony Road, Toronto, Ontario (CA), M2L 2K1

(73) Assignee: Bernard Charles Sherman, Toronto (CA)

( * ) Notice: Subject to any disclaimer, the term of this patent is extended or adjusted under 35 U.S.C. 154(b) by 0 days.

(21) Appl. No.: 10/129,622

(22) PCT Filed: Aug. 4, 2000

(86) PCT No.: PCT/CA00/00901

§ 371 (c)(1), (2), (4) Date: May 9, 2002

(87) PCT Pub. No.: WO01/36409

PCT Pub. Date: May 25, 2001

(30) Foreign Application Priority Data

Nov. 16, 1999 (CA) ................................................ 2290893

(51) Int. Cl.⁷ ..................... A61K 401/12; C07D 401/12
(52) U.S. Cl. ..................................... 514/338; 546/273.7
(58) Field of Search ........................ 514/338; 546/273.7

(56) References Cited

FOREIGN PATENT DOCUMENTS

| CA | 2166794 | 1/1995 |
|---|---|---|
| CA | 2254572 | 10/1999 |
| EP | 0 005 129 | 10/1979 |
| EP | 0 124 495 | 11/1984 |
| WO | WO 95/01977 | 1/1995 |
| WO | WO 96/01623 | 1/1996 |
| WO | WO 97/41114 | 11/1997 |
| WO | WO 00/30612 | 11/1999 |
| WO | WO 00/30612 | 6/2000 |
| WO | WO 01/87831 | * 11/2001 |

OTHER PUBLICATIONS

CA 95:25045, Min et al. 1995.*
CA 95:16153, Neises et al.1995.*

* cited by examiner

Primary Examiner—Patricia L. Morris
(74) Attorney, Agent, or Firm—Neil H. Hughes; Ivor M. Hughes

(57) ABSTRACT

Improved process to produce magnesium omeprazole substantially amorphous with pharmaceutically acceptable low level of methanol and solid pharmaceutical compositions.

13 Claims, No Drawings

MAGNESIUM OMEPRAZOLE

This application is the US national phase of international application PCT/CA00/00901 filed Aug. 4, 2000 which designated the U.S.

FIELD OF THE INVENTION

The present invention relates to an improved form of magnesium omeprazole, a process for making same, and pharmaceutical compositions same.

BACKGROUND OF THE INVENTION

The compound known under the generic name omeprazole is described in European patent 0005129.

Omeprazole is useful for inhibiting gastric acid secretion and has gastric mucosa protective activity in mammals and man. Omeprazole may be used for prevention and treatment of gastric acid related disorders and gastrointestinal inflammatory diseases in mammals and man, including for example gastritis, gastric ulcer and duodenal ulcer.

The term "omeprazole" as used in this specification designates the neutral form of the compound, that is the form without a salt-forming cation present.

Certain salts of omeprazole are described in European patent 0124495.

In EP 0124495, example 5 specifically discloses the synthesis of magnesium omeprazole dihydrate, and example 6 specifically discloses the synthesis of magnesium omeprazole anhydrate. Manufacturing of the described magnesium omeprazole salts presents significant difficulties.

The process of manufacture and isolation of the dihydrate according to example 5 is relatively complex. It requires making the sodium salt, adding a solution of magnesium chloride to obtain a precipitate, removing water by centrifuging the precipitate, washing the precipitate with deionized water until no Cl⁻ is detectable, drying in air, grinding, and the drying in vacuum at 40° C. for 24 h. Moreover, because the resulting magnesium omeprazole dihydrate is crystalline, the rate of dissolution in intestinal fluid is relatively slow, unless the material is milled to a relatively fine particle size.

The process of making the anhydrate according to example 6 is simpler. Magnesium is reacted with methanol to give a solution of magnesium methoxide in methanol. The solution is added to a solution of omeprazole in methanol, the quantity of omeprazole being one mole for each two moles of magnesium. The methanol is then evaporated to give a crystalline solid, which is magnesium omeprazole anhydrate. However, the anhydrate as made by this process is also not without a problem. As the magnesium omeprazole precipitates from the solution upon evaporation of the methanol, residual methanol is entrapped in the solid particles and cannot easily be removed by evaporation. Methanol is toxic and high levels are generally considered unacceptable in pharmaceutical chemicals.

Canadian patent 2166794 describes what is said to be an improved form of magnesium omeprazole dihydrate, which has a higher degree of crystallinity than that of example 5 of EP 0124495. This form has a methanol content of less than 0.1%. However, like the product of example 6 of EP 0124495, it is a crystalline dihydrate, and the process of manufacture is relatively complex. According to Canadian patent 2166794, the degree of crystallinity of a sample made according to example 6 of EP 0124495 was 67%, whereas the degree of crystallinity of the improved form is at least 70%.

Canadian patent application No. 2254572 discloses improved processes for the production of magnesium omeprazole crystalline dihydrate. The disclosure reviews the prior art, and in particular, in relation to the anhydrate of example 6 of EP 0124495, states as follows: "This procedure cannot be practised on a large scale because of the need to evaporate to dryness. It has been found that unacceptable and potentially dangerous amounts of methanol become trapped in this solid, making it pharmaceutically unacceptable." The processes of Canadian patent 2254572 are again relatively complex.

Improved processes for the production of magnesium omeprazole crystalline dihydrate are also described in PCT Publication No. WO 97/4114. The degree of crystallinity of the product of example 1 is said to be 80%. Again, the processes disclosed are relatively complex.

In summary, the only magnesium omeprazole according to the prior art that has an acceptably low level of methanol is magnesium omeprazole crystalline dihydrate, which has a degree of crystallinity of 67% or higher and is produced only by relatively complex processes.

In light of the foregoing, the object of the present invention is to produce magnesium omeprazole that has acceptably low levels of methanol, but is substantially amorphous (non-crystalline), and can be produced by a simple process.

BRIEF SUMMARY OF THE INVENTION

Magnesium omeprazole of the present invention is made by reacting magnesium in a lower alcohol to form magnesium alkoxide, adding omeprazole in a quantity of about two moles per mole of magnesium, and flash-evaporating the alcohol, so as to form a solid precipitate without allowing the growth of crystals or particles that entrap the alcohol at unacceptable levels. The resulting material is substantially amorphous (non-crystalline).

DETAILED DESCRIPTION OF THE INVENTION

In the process of manufacture of magnesium omeprazole according to the present invention, magnesium is reacted in a lower alcohol, preferably methanol, to form a solution of magnesium alkoxide in the alcohol.

The atomic weight of magnesium is 24.3 and the molecular weight of omeprazole is 345.4. Since magnesium is divalent, the amount of magnesium required to convert 345.4 grams of omeprazole to magnesium omeprazole is 12.15 grams.

Hence 35.2 grams of magnesium is needed to convert 1 kilo of omeprazole to magnesium omeprazole.

The process of converting 1 kilo of omeprazole to magnesium omeprazole thus begin with reacting 35.2 grams of magnesium in a lower alcohol, preferably methanol. The minimum amount of methanol needed to fully react and dissolve 35.2 grams of magnesium is about 1000 grams.

When the magnesium is immersed in the alcohol, the reaction will be evident from the generation of hydrogen bubbles, and the reaction will be complete when all the magnesium has been consumed and the effervescence has ceased. All of the magnesium will then be present as magnesium alkoxide in the alcohol (i.e. magnesium methoxide in methanol, if methanol is used as the alcohol).

The omeprazole can then added directly to the magnesium alkoxide solution. Attentively, the omeprazole may first be dissolved in an alcohol or another organic solvent that is miscible with the alcohol used to make the magnesium alkoxide, and the resultant solution may then be added to the magnesium alkoxide solution.

Where methanol is used as the sole solvent, a total of only about 1.5 kilos is needed for converting 1 kilo of omeprazole to magnesium omeprazole in solution by the methanol.

Hence, using quantities based on 1 kilo of omeprazole, the simplest and best procedure is to react 35.2 grams of magnesium in about 1.5 kilos of methanol, wait until the magnesium has been fully reacted, and then add the 1 kilo of omeprazole to the solution and stir to dissolve. The resulting solution will be a solution of magnesium omeprazole equivalent to 1 kilo of omeprazole in methanol.

In order to obtain solid magnesium omeprazole that is substantially free of organic solvent (i.e. substantially free of methanol, if methanol is used), it is then necessary to eliminate the solvent.

It has been found that this can be done by "flash-evaporating" the solvent. Flash-evaporating will be understood to mean evaporating in such a way as to avoid the precipitation of crystals or large particles which entrap the alcohol.

One method of flash-evaporating the solvent is to mix the solution into a solid excipient such as, for example, microcrystalline cellulose so that a damp mass is formed. The mass can then be dried in a conventional oven, a fluid bed drier, or under vacuum to remove the solvent. Because the solution has been dispersed throughout the solid excipient, as the solvent evaporates, the omeprazole magnesium is deposited as a thin layer over the surface of the particles of the solid excipient and does not precipitate as crystals or large granules, so that there is little or no entrapment of solvent.

The preferred way of flash-evaporating the solvent is by spray-drying the solution.

It has been found that, by such process, magnesium omeprazole can be made having a residual solvent content substantially lower than can be achieved by simply evaporating the solvent from the solution under vacuum.

The residual organic solvent content by weight of the magnesium omeprazole made according to the present invention will be under 7%, preferably under 5%, more preferably under 2%, and most preferably under 1%.

The degree of crystallinity of the obtained product can be measured with powder X-ray diffraction (XRD) as described in WO97/4114 as follows: A thin layer of the triturated sample is smeared onto a cut silicon single crystal zero background holder which is rotated during the measurement. Cu Kα radiation and constant or automatic antiscatter and divergence slits are used to obtain a diffractogram with 2θ from 1 or 2° to at least 35°.

The degree of crystallinity is calculated with the formula degree of crystallinity=100+$C/(A+C)$ C=the area from the peaks in the diffractogram ("the crystalline area"), A=the area between the peaks and the background ("the amorphous area").

Area calculations are performed for 2θ between 4–33°. The lowest intensity value found in this interval is chosen as the constant background and subtracted from the area A. When constant slits are used, the increased background at low angles due to the influence from the primary beam is also subtracted from the area A.

The degree of crystallinity of magnesium omeprazole according to the present invention is under 67%, as compared to 67% or higher for magnesium omeprazole crystalline dihydrate according to the prior art.

The degree of crystallinity will preferably be under 60%, more preferably under 50%, and most preferably under 25%.

If the magnesium omeprazole of the present invention is made in an environment and using excipients (including the air or other gas used for drying in the spray-dry process) that is completely free of water, the magnesium omeprazole will be anhydrous. However, pure anhydrous magnesium omeprazole is hygroscopic and it will readily absorb water from air until it reaches an equilibrium water content of about 5% to 8%, depending on the relative humidity of the air. This is not problematic, as it does not adversely affect stability.

The magnesium omeprazole of the present invention will be further processed into pharmaceutical compositions such as, for example, tablets for oral administration. The tablets will preferably be enteric coated to protect the magnesium omeprazole from the effects of gastric acid.

The invention will be further understood from the following examples, which are intended to be illustrative and not limiting of the invention.

EXAMPLE 1

1.76 g of pure magnesium was added to 800 g of methanol in a 1000 mL glass flask. The flask was closed with a loose-fitting stopper (loose to allow hydrogen gas to escape), and the flask was allowed to sit overnight.

The next morning it was observed that the magnesium had all been consumed and that the effervescence had ceased, resulting in a slightly hazy solution of magnesium methoxide in methanol. 50 grams of omeprazole was then added to the contents of the flask and the contents were stirred for several minutes until the omeprazole dissolved to form a solution of magnesium omeprazole in methanol.

EXAMPLE 2

To produce a reference sample of magnesium omeprazole anhydrate according to the prior art (i.e. example 6 of EP 0124495), about 20% of the solution from step 2 was transferred to a 1000 mL beaker. The beaker was then placed in a vacuum oven for drying under vacuum at 50° C. for a period of 4 hours. At the end of this time, a solid material remained that had no evident odour of residual methanol. This solid material was tested to determine the level of residual methanol, which was found to be 7.2% by weight.

EXAMPLE 3

To produce magnesium omeprazole of the present invention, the balance of the solution of Example 1 was spray-dried on a Yamato® spray-dryer, using an inlet air temperature of about 140° C. and outlet air temperature of about 70° C.

The resulting dry material was a fine powder, which appeared non-crystalline and also had no evident odour of residual methanol. The powder was tested to determine the level of residual methanol, which was found to be 0.7%.

This powder was examined for crystallinity by powder X-ray diffraction, and it was found that the powder was substantially amorphous (non-crystalline), having a degree of crystallinity of under 25%.

EXAMPLE 4

The following ingredients were mixed together in the proportions shown:

| | |
|---|---|
| Magnesium omeprazole | 21. |
| Anhydrous lactose | 131. |
| Croscarmellose sodium | 6.4 |
| Magnesium stearate | 1.6 |
| | 160. |

The mixture was compressed into tablets having a weight of 160 mg per tablet, so that each tablet contained 21 mg of magnesium omeprazole, which is equivalent to about 20 mg of omeprazole.

A sub-coating comprising hydroxypropyl methylcellulose dissolved in water was then applied to the tablets by spray-application in a side-vented coating pan.

An enteric coating was then applied over the sub-coating by spray-application of methacrylic acid copolymer aqueous dispersion, with triethyl citrate dissolved therein as plasticizer.

What is claimed is:

1. A process of producing magnesium omeprazole, said process comprising the steps of:
   (i) reacting magnesium with a lower alcohol to produce magnesium alkoxide in solution in the lower alcohol as solvent,
   (ii) adding omeprazole to the solution, the amount of omeprazole being about 2 moles per mole of magnesium, and
   (iii) flash-evaporating the solvent yielding magnesium omeprazole having a degree of crystallinity of under 67% by weight and having a residual organic solvent content of less than 7% by weight.

2. A process of claim 1 wherein the lower alcohol is methanol.

3. A process of claim 1 wherein the flash-evaporation is done by spray-drying the solution.

4. Magnesium omeprazole having a degree of crystallinity of under 67% by weight and having a residual organic solvent content of less than 7% by weight.

5. Magnesium omeprazole of claim 4 having a residual organic solvent content of less than 5% by weight.

6. Magnesium omeprazole of claim 4 having a residual organic solvent content of less than 2% by weight.

7. Magnesium omeprazole of claim 4 having a residual organic solvent content of less than 1% by weight.

8. Magnesium omeprazole of claim 4 having a degree of crystallinity of under 60%.

9. Magnesium omeprazole of claim 4 having a degree of crystallinity of under 50%.

10. Magnesium omeprazole of claim 4 having a degree of crystallinity of under 25%.

11. A solid pharmaceutical composition for oral administration comprising magnesium omeprazole of claim 4.

12. A composition of claim 11 in the form of that tablet.

13. A composition of claim 12 wherein the tablet is enteric coated.

* * * * *